United States Patent
Mine et al.

[11] Patent Number: 6,133,469
[45] Date of Patent: Oct. 17, 2000

[54] ANTI-FERROELECTRIC LIQUID CRYSTAL COMPOUND

[75] Inventors: Takakiyo Mine; Masahiro Johno; Tomoyuki Yui, all of Tsukuba, Japan

[73] Assignee: Mitsubishi Gas Chemical Company, Tokyo, Japan

[21] Appl. No.: 09/365,843

[22] Filed: Aug. 3, 1999

[30] Foreign Application Priority Data

Aug. 7, 1998 [JP] Japan .................................. 10-224768

[51] Int. Cl.[7] ........................... C07C 69/76; C09K 19/12
[52] U.S. Cl. ................................ 560/59; 560/62; 560/65; 252/299.65
[58] Field of Search ................... 560/59, 62, 65

[56] References Cited

U.S. PATENT DOCUMENTS 5,972,243  10/1999  Mine et al. ....................... 252/299.65

FOREIGN PATENT DOCUMENTS

| | | |
|---|---|---|
| 0342046 | 11/1989 | European Pat. Off. |
| 0450595 | 10/1991 | European Pat. Off. |
| 0582468 | 2/1994 | European Pat. Off. |
| 0718274 | 12/1995 | European Pat. Off. |
| 0853076 | 1/1998 | European Pat. Off. |
| 0893429 | 1/1999 | European Pat. Off. |
| 643154 | 1/1989 | Japan . |
| 1213390 | 8/1989 | Japan . |
| 1316339 | 12/1989 | Japan . |
| 1316367 | 12/1989 | Japan . |
| 1316372 | 12/1989 | Japan . |
| 228128 | 1/1990 | Japan . |
| 2225434 | 9/1990 | Japan . |
| 2229128 | 9/1990 | Japan . |

OTHER PUBLICATIONS

A.D.L. Chandani, et al., "Tristable switching in Surface Stabilized . . . ", Japanese Journal of Applied Physics, vol. 27, No. 5, May, 1988, pp. 729–732.

A.D.L. Chandani, et al., "Novel Phase Exhibiting Tristable Switching . . . ", Japanese Journal of Applied Physics, vol. 28, No. 7, Jul., 1989, pp. 1261–1264.

Masahiro Johno, et al., "Smectic Layer Switching by an Electric Field . . . ", Japanese Journal of Applied Physics, vol. 28, No. 1, Jan., 1989, pp. 119–120.

A.D.L. Chandani, et al., "Antiferroelectric Chiral Smectic Phases . . . ", Japanese Journal of Applied Physics, vol. 28, No. 7, Jul., 1989, pp. 1265–1268.

Masahiro Johno, et al., "Correspondence between Smectic Layer Switching . . . " Japanese Journal of Applied Physics, vol. 29, No. 1, Jan., 1990, pp. 111–114.

Y. Suzuki, et al., "New Fluorine–containing ferroelectric liquid . . . ", Liquid Crystals, 1989, vol. 6, No. 2, pp. 167–174.

*Primary Examiner*—Gary Geist
*Assistant Examiner*—Leigh C. Maier

[57] ABSTRACT

A novel anti-ferroelectric liquid crystal compounds of the formula (1),

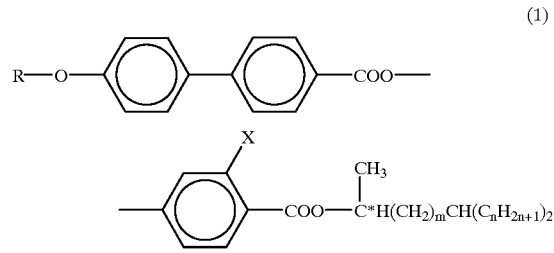

wherein R is a linear alkyl group having 6 to 12 carbon atoms, X is a hydrogen atom or a fluorine atom, m is an integer of 1 to 3, n is an integer of 1 or 2, and C* is an asymmetric carbon atom.

The above anti-ferroelectric liquid crystal compounds have an anti-ferroelectric phase in a broad temperature range, so that they can be advantageously used as a main component for a liquid crystal material for practical use or as a component for a liquid crystal composition.

8 Claims, No Drawings

ANTI-FERROELECTRIC LIQUID CRYSTAL COMPOUND

FIELD OF THE INVENTION

The present invention relates to a novel anti-ferroelectric liquid crystal compound.

PRIOR ART

A liquid crystal display device has been so far used mainly for various small-sized display devices owing to its operability at low voltage, low electric power consumption and performance of display with a thin screen. However, with recent increase in the application and use of liquid crystal display devices to/in the fields of information and office automation-related machines and equipment and the field of television sets, there are rapidly increasing demands for large-sized and high performance liquid crystal display devices having larger display capacity and higher display quality than those of existing CRT display devices.

However, so long as a nematic liquid crystal available at present is used in a display device, even an active matrix driven liquid crystal display device (TFT) used in a liquid crystal television set finds it not easy to increase its size and decrease its production cost due to its complicated production process and a low yield. In a simple matrix driven STN liquid crystal display device (STN), too, the driving of a large-capacity display device is not necessarily easy and its response time is limited, and hence, display of video frames is difficult to obtain. At present, therefore, it cannot at all be said that the nematic liquid crystal display device can satisfy demands toward the above high-performance large-sized liquid crystal display device.

As for display quality, further, either of TFT and STN display devices using a nematic liquid crystal have a serious problem in that the viewing angle is narrow. Though various improvement measures have been proposed, it is difficult to find out a drastic improvement measure so long as a nematic liquid crystal is used.

Under the circumstances, a liquid crystal display device for which a ferroelectric liquid crystal is used is attracting attention as a liquid crystal display device with a fast response speed and a wide viewing angle. A surface-stabilized ferroelectric liquid crystal (SSFLC) device disclosed by Clark and Lagerwall comes to notice in that it has a fast response speed and a wide viewing angle which have not been achieved in the past. Its switching characteristics have been studied in detail, and a number of ferroelectric liquid crystal compounds have been synthesized for optimizing various physical property constants.

When a ferroelectric liquid crystal is used as a liquid crystal display device, however, a special devising with regard to the alignment of the liquid crystal is required for achieving a practically acceptable contrast, because its threshold characteristic is insufficient and its layer has a chevron structure. Further, since the alignment of its liquid crystal molecules is extremely difficult to control, it is not easy to attain the bistability, which is one of the most important characteristics of SSFLC, with good reproducibility.

Further, there is another problem that when the alignment of the liquid crystal molecules is damaged by a mechanical shock, it is difficult to restore its alignment. It is, therefore, essentially required to overcome these problems in order to put the display device to practical use.

PROBLEMS TO BE SOLVED BY THE INVENTION

As described above, efforts have been made in various ways to develop novel modes for increasing the size of a liquid crystal display device and achieving a liquid crystal display device with finer definition. Under the circumstances, development of display devices having switching mechanisms far different from the prior devices is also under way simultaneously.

Switching among three stable states of a liquid crystal compound having an anti-ferroelectric phase (to be referred to as "anti-ferroelectric liquid crystal compound" hereinafter) is one of these new switching mechanisms (Japanese Journal of Applied Physics, Vol. 27, pp. L729, 1988).

The anti-ferroelectric liquid crystal device has three stable states, i.e., two uniform states (Ur, Ul) observed in a ferroelectric liquid crystal device and a third state. Chandani et al. report that the above third state is an anti-ferroelectric phase (Japanese Journal of Applied Physics, vol. 28, pp. L1261, 1989; ditto, pp. L1265). The above switching among three stable states is the first characteristic of an anti-ferroelectric liquid crystal device.

The second characteristic of the anti-ferroelectric liquid crystal device is that a sharp threshold value exists in respect to an applied voltage.

Further, the anti-ferroelectric liquid crystal device has a memory effect, and this is the third characteristic of the anti-ferroelectric liquid crystal device.

By utilizing the above excellent characteristic features, a liquid crystal display device having a fast response speed and a good contrast can be materialized.

The anti-ferroelectric liquid crystal device has another important characteristic in that its layer structure easily performs switching when an electric field is applied (Japanese Journal of Applied Physics, Vol. 28, pp. L119, 1989; ditto, vol. 29, pp. L111, 1990).

On the basis of the anti-ferroelectric liquid crystal device having the above characteristics, a liquid crystal display device having very few defect and the capability to self-restoring a molecule alignment can be produced, and a liquid crystal display device having an excellent contrast can be achieved.

As an anti-ferroelectric liquid crystal compound, there are known compounds disclosed in JP-A-1-213390, JP-A-1-316339, JP-A-1-316367, JP-A-1-316372, JP-A-2-28128 and "Liquid Crystals", Vol. 6, pp. 167 (1989). Though the number of anti-ferroelectric liquid crystal compounds that have been so far known is not so large as that of ferroelectric liquid crystal compounds, anti-ferroelectric liquid crystal compounds are increasing in number with the advance in studies thereof.

In the field of ferroelectric liquid crystals, attempts are being energetically made to synthesize ferroelectric liquid crystal compounds from the following alcohols in which a fluoroalkyl group is substituted on an asymmetric carbon atom, as an optically active alcohol for the synthesis (e.g., see JP-A-64-3154, JP-A-1-316339, JP-A-1-316367, JP-A-1-316372, JP-A-2-225434 and JP-A-2-229128).

(1) $CF_3C^*H(OH)CH_2COOC_2H_5$ (2) $CF_3C^*H(OH)CH_2CH_2OC_2H_5$ (3) $CF_3C^*H\ (OH)\ CH_2CH_2CH_2OC_2H_5$ (4) $CF_3C^*H(OH)C_6H_{13}$ (5) $CF_3C^*H(OH)C_8H_{17}$ (6) $C_2F_5C^*H(OH)C_8H_{17}$

All of ferroelectric liquid crystals derived from the above alcohols have a substituted fluoroalkyl group having a high electronegativity, on the asymmetric carbon atom and hence, give high spontaneous polarization and also give a relatively fast response speed. Especially, it is known that liquid crystal compounds derived from the above optically active alcohols (4), (5) and (6) easily give liquid crystal compounds having an anti-ferroelectric phase.

On the other hand, from the viewpoint of practical use, the requirements of a liquid crystal are that it has an anti-ferroelectric phase in a broad temperature range and has a low melting point.

The present invention has been made from the above points of view and has been accomplished by finding out that a triphenyl ester-containing liquid crystal obtained from an optically active alcohol having a methyl group on an asymmetric carbon atom and a terminal branched alkyl groups having the same numbers of carbon atoms gives an anti-ferroelectric liquid crystal compound having an anti-ferroelectric phase in a broad temperature range.

MEANS TO SOLVE THE PROBLEMS

That is, according to the present invention, there is provided an anti-ferroelectric liquid crystal compound of the following formula (1),

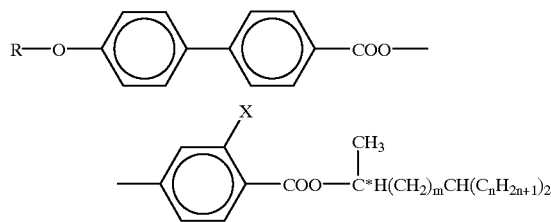

(1)

wherein R is a linear alkyl group having 6 to 12 carbon atoms, X is a hydrogen atom or a fluorine atom, m is an integer of 1 to 3, n is an integer of 1 or 2, and C* is an asymmetric carbon atom.

The anti-ferroelectric liquid crystal compound of the present invention is represented by the above formula (1), in which R is a linear alkyl group having 6 to 12 carbon atoms, preferably a linear alkyl group having 8 to 12 carbon atoms. X is a hydrogen atom or a fluorine atom, and preferably is a fluorine atom. m is an integer of 1 to 3. Further, n is an integer of 1 or 2. Particularly, a compound of the formula (1) in which R is a linear alkyl group having 9 carbon atoms is preferred because it has a stable anti-ferroelectric phase in the broad temperature range, and it can be effectively used as the main component or additive component in an anti-ferroelectric liquid crystal composition.

The optically active alcohol, $CH_3C^*H(OH)(CH_2)_mCH(C_nH_{2n+1})_2$, used for the synthesis of the above anti-ferroelectric liquid crystal compound of the present invention can be easily produced by the method that the present inventors already proposed. The method of the production thereof in the case, for example, when m is 1 and n is 1 in the formula (1), is outlined as follows.

(a)

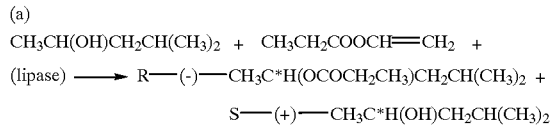

(b)

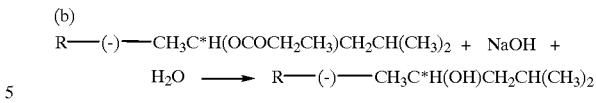

The above reaction scheme will be briefly explained as follows.

(a) shows an asymmetric esterification reaction between a commercially available 4-methylpentan-2-ol and vinyl propionate.

(b) shows the hydrolysis reaction of the optically active ester obtained in the (a) by alkali.

EFFECT OF THE INVENTION

The present invention provides a novel anti-ferroelectric liquid crystal compound. The novel anti-ferroelectric liquid crystal compound provided by the present invention has anti-ferroelectric phase in a broad temperature range, and can be advantageously used as the main component of a liquid crystal material for practical use or as a component of a liquid crystal composition.

EXAMPLES

The present invention will be explained more in detail with reference to Examples hereinafter, while the present invention shall not be limited to these Examples.

Example 1

Preparation of R-(−)-3-fluoro-4-(1,3-dimethylbutyloxycarbonyl)phenyl-4'-n-nonyloxybiphenyl-4-carboxylate (E1) (R=$C_9H_{19}$, X=F, m=1, n=1 in the formula (1))

(1) Preparation of 4-(4'-n-hexyloxy)biphenylcarboxylic acid 10.0 Grams of 4-(4'-hydroxy)biphenylcarboxylic acid and 12.0 g of n-nonyl bromide were added to a mixture containing 1,500 ml(milliliters) of ethanol and 200 ml of water, and the mixture was allowed to react under reflux for 10 hours. 500 ml of water was further added thereto, and the resultant mixture was stirred for 3 hours.

After completion of the reaction, the reaction mixture was acidified by adding concentrated hydrochloric acid, 500 ml of the solvent was distilled off, and the residue was cooled to room temperature to give a white solid. The white solid was fully washed with water and then re-crystallized from chloroform, to give 12.8 g of an end product in the form of a white crystal.

(2) Preparation of 4-acetoxy-2-fluorobenzoic acid 4.3 Grams of 2-fluoro-4-hydroxybenzoic acid and 8.4 g of anhydrous acetic acid were placed in a two-necked flask, and mixed. 5 Drops of sulfuric acid were added to the mixture under cooling with water. After heat generation ended, the mixture was heated at 80° C. for 30 minutes. Thereafter, the reaction mixture was poured into cold water, and a precipitated crystal was recovered by filtration. The crystal was dried in vacuum, and used in the next step.

(3) Preparation of R-(−)-4-acetoxy-2-fluoro-1-(1,3-dimethyl-butyloxycarbonyl)benzene 1.0 Gram of 4-acetoxy-2-fluorobenzoic acid was added to 7 ml of thionyl chloride, and the mixture was allowed to react under reflux for 5 hours. Then, after excessive thionyl chloride was distilled off, a mixture containing 1 ml of pyridine, 4 ml of dry ether and 0.6 g of R-(−)-4-methyl-pentan-2-ol was dropwise added thereto. After the addition, the mixture was stirred at room temperature for one day and night and diluted with 200 ml of ether. An organic layer was washed with diluted hydrochloric acid, with a 1N sodium hydroxide aqueous solution and with water in this order, and dried over magnesium sulfate. The solvent was distilled off, and the resulting crude product was purified by a silica gel column chromatography using hexane/ethyl acetate as a solvent, to give an end product.

(4) Preparation of R-(−)-4-hydroxy-2-fluoro-1-(1,3-dimethylbutyloxycarbonyl)benzene 1.0 Gram of the compound obtained in the above (3) was dissolved in 30 ml of ethanol, and 3 g of benzylamine was added dropwise. Further, after the mixture was stirred at room temperature for one day and night, it was diluted with 300 ml of ether, washed with diluted hydrochloric acid and then with water in this order, and dried over magnesium sulfate. The solvent was distilled off, and the residue was subjected to silica gel column chromatography for isolation and purification, to give an end product.

(5) Preparation of R-(−)-3-fluoro-4-(1,3-dimethyl-butyloxycarbonyl)phenyl-4'-n-nonyloxybiphenyl-4-carboxylate To 1.0 g of the compound obtained in the above (1) was added to 10 ml of thionyl chloride, and the mixture was refluxed under heating for 10 hours. Excessive thionyl chloride was distilled off and then 10 ml of pyridine and 25 ml of toluene were added to the mixture. Thereafter, 25 ml of a benzene solution containing 0.8 g of the compound obtained in the above (4) was added dropwise, and the mixture was allowed to react at room temperature for 10 hours.

After completion of the reaction, the reaction mixture was diluted with 300 ml of ether, washed with diluted hydrochloric acid, with a 1N sodium carbonate aqueous solution and with water in this order, and an organic layer was dried over magnesium sulfate.

Then, the solvent was distilled off, the residue was isolated by silica gel column chromatography and re-crystallized from ethanol to give an end product.

Example 2

Preparation of R-(−)-3-fluoro-4-(1-methyl-3-ethylpentyloxycarbonyl)phenyl-4'-n-nonyloxybiphenyl-4-carboxylate (E2) (R=$C_9H_{19}$, X=F, m=1, n=2 in the formula (1))

An end product was obtained in the same manner as in Example 1 except that 4-ethylhexan-2-ol was used in place of 4-methylpentan-2-ol.

Example 3

Preparation of R-(−)-3-fluoro-4-(1,3-n-dimethyl-butyloxycarbonyl)phenyl-4'-octyloxybiphenyl-4-carboxylate (E3) (R=$C_8H_{17}$, X=F, m=1, n=1 in the formula (1))

An end product was obtained in the same manner as in Example 1 except that 4-(4'-n-octyloxy)biphenylcarboxylic acid was used in place of 4-(4'-n-nonyloxy)biphenylcarboxylic acid.

Example 4

Preparation of R-(−)-3-fluoro-4-(1,3-dimethyl-butyloxycarbonyl)phenyl-4'-n-dodecyloxybiphenyl-4-carboxylate (E4) (R=$C_{12}H_{25}$, X=F, m=1, n=1 in the formula (1))

An end product was obtained in the same manner as in Example 1 except that 4-(4'-n-dodecyloxy)biphenylcarboxylic acid was used in place of 4-(4'-n-nonyloxy)biphenylcarboxylic acid.

Example 5

Preparation of R-(−)-3-fluoro-4-(1,5-dimethyl-hexyloxycarbonyl)phenyl-4'-n-nonyloxybiphenyl-4-carboxylate (E5) (R=$C_9H_{19}$, X=F, m=3, n=1 in the formula (1))

An end product was obtained in the same manner as in Example 1 except that R-(−)-6-methylheptan-2-ol was used in place of R-(−)-4-methylpentan-2-ol.

The general formula of the liquid crystal compounds obtained in Examples 1 to 5 is shown under Table 1, and their NMR data are shown in Table 1.

The identification of the liquid crystal phase was made by texture observation and measurement with DSC (differential scanning calorimeter). The results are shown also in Table 2.

TABLE 1

| Hydrogen atom No.: | Chemical shift (ppm) | | | | | | | | |
| --- | --- | --- | --- | --- | --- | --- | --- | --- | --- |
| | 1H | 2H | 3H | 4H | 5H | 6H | 7H | 8H | 9H |
| Example 1 (E1) | 4.0 | 7.0 | 7.6 | 7.7 | 8.2 | 7.2 | 7.2 | 8.0 | 5.2 |
| Example 2 (E2) | 4.0 | 7.0 | 7.6 | 7.7 | 8.2 | 7.2 | 7.2 | 8.0 | 2.2 |
| Example 3 (E3) | 4.0 | 7.0 | 7.6 | 7.7 | 8.2 | 7.2 | 7.2 | 8.0 | 5.2 |
| Example 4 (E4) | 4.0 | 7.0 | 7.6 | 7.7 | 8.2 | 7.2 | 7.2 | 8.0 | 5.2 |
| Example 5 (E5) | 4.0 | 7.0 | 7.6 | 7.7 | 8.2 | 7.2 | 7.2 | 8.0 | 5.2 |

TABLE 1-continued

| | Chemical shift (ppm) | | | | | | | | |
|---|---|---|---|---|---|---|---|---|---|
| Hydrogen atom No.: | 1H | 2H | 3H | 4H | 5H | 6H | 7H | 8H | 9H |

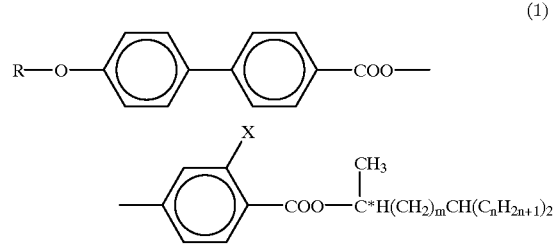

(p is an integer of 4 to 10)

TABLE 2

| | Phase sequence |
|---|---|
| Example 1 (E1) | I(142)SA(131)SCA*(18)SX(-18)Cr |
| Example 2 (E2) | I(119)SA(112)SCA*(7)SX(<-10)Cr |
| Example 3 (E3) | I(145)SA(130)SCγ*(103)SCA*(32)Cr |
| Example 4 (E4) | I(131)SA(122)SCA*(6)Cr |
| Example 5 (E5) | I(134)SA(125)SC*(122)SCA*(17)SX(-21)Cr |

In the phase sequence, parenthesized values show phase transition temperatures (° C.), I is an isotropic phase, SA is a smectic A phase, SC γ* is a ferrielectric phase, SCA* is an anti-ferroelectric phase, SC* is a ferroelectric phase, SX is an unknown phase and Cr is a crystal phase, respectively.

What is claimed is:

1. An anti-ferroelectric liquid crystal compound of the following formula (1):

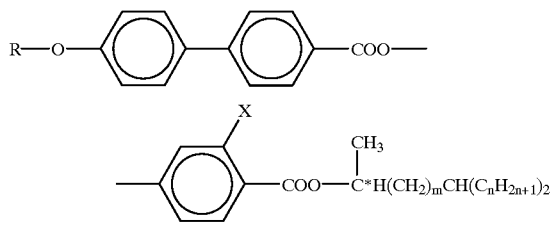

wherein R is a linear alkyl group having 6 to 12 carbon atoms, X is a fluorine atom, m is an integer of 1 or 3, n is an integer of 1 or 2, and C* is an asymmetric carbon atom.

2. The anti-ferroelectric liquid crystal compound of claim 1, wherein R in the formula (1) is a linear alkyl group having 8 to 12 carbon atoms.

3. The anti-ferroelectric liquid crystal compound according to claim 1, wherein m is 1.

4. An anti-ferroelectric liquid crystal compound of the following formula (1):

wherein R is a linear alkyl group of 6 to 12 carbon atoms, X is a hydrogen atom or a fluorine atom, m is 1, n is 1 or 2, and C* is an asymmetric carbon atom.

5. The anti-ferroelectric liquid crystal compound of claim 4, wherein, R is n-nonyl, X is F, m is 1 and n is 1 or 2.

6. The anti-ferroelectric liquid crystal compound according to claim 5, wherein n is 1.

7. The anti-ferroelectric liquid crystal compound according to claim 5, wherein n is 2.

8. An anti-ferroelectric liquid crystal compound which is a member selected from the group consisting of R-(-)-3-fluoro-4-(1,3-dimethylbutyloxycarbonyl)phenyl-4'-n-nonyloxybiphenyl-4-carboxylate, R-(-)-3-fluoro-4-(1-methyl-3-ethylpentyloxycarbonyl)phenyl-4'-n-nonyloxybiphenyl-4-carboxylate, R-(-)-3-fluoro-4-(1,3-n-dimethyl-butyloxycarbonyl)phenyl-4'-octyloxybiphenyl-4-carboxylate, R-(-)-3-fluoro-4-(1,3-dimethyl-butyloxycarbonyl)phenyl-4'-n-dodecyloxybiphenyl-4-carboxylate, and R-(-)-3-fluoro-4-(1,5-dimethyl-hexyloxycarbonyl)phenyl-4'-n-nonyloxybiphenyl-4-carboxylate.

* * * * *